(12) United States Patent
Causton et al.

(10) Patent No.: US 6,703,006 B2
(45) Date of Patent: Mar. 9, 2004

(54) DEODORANT COMPOSITIONS

(75) Inventors: Brian Edward Causton, Reading (GB); Sydney Christopher Tavern, Reading (GB)

(73) Assignee: The Gillette Company, Boston, MA (US)

( * ) Notice: Subject to any disclaimer, the term of this patent is extended or adjusted under 35 U.S.C. 154(b) by 127 days.

(21) Appl. No.: 09/938,268

(22) Filed: Aug. 23, 2001

(65) Prior Publication Data

US 2002/0146377 A1 Oct. 10, 2002

Related U.S. Application Data

(63) Continuation of application No. PCT/US00/04497, filed on Feb. 23, 2000.

(51) Int. Cl.[7] .............................. A61K 7/32; A61K 7/36; A61K 7/00; C01G 9/00; C01G 9/02
(52) U.S. Cl. .......................... 424/65; 423/99; 423/622; 424/67; 424/400; 424/401
(58) Field of Search ........................... 424/65, 67, 400, 424/401; 423/99, 622

(56) References Cited

U.S. PATENT DOCUMENTS

| | | | |
|---|---|---|---|
| 3,984,591 A | 10/1976 | Plumat et al. | 427/165 |
| 4,289,816 A | 9/1981 | Fogelberg et al. | 428/35 |
| 5,122,418 A | 6/1992 | Nakane et al. | 424/401 |
| 5,182,318 A | 1/1993 | Savin | 523/216 |
| 5,306,522 A | 4/1994 | Clough et al. | 427/126.3 |
| 5,407,743 A | 4/1995 | Clough et al. | 428/357 |
| 5,531,985 A | 7/1996 | Mitchell et al. | 424/59 |

FOREIGN PATENT DOCUMENTS

| | | |
|---|---|---|
| EP | 0333118 | 9/1989 |
| EP | 0459003 | 12/1991 |
| EP | 0572914 | 12/1993 |

OTHER PUBLICATIONS

Ambia, M.G., et al. "The effects of deposition variables on the spray pyrolysis of ZnO thin film" Journal of Materials Science, vol. 29, pp. 6575–6580, (1994).
Cinibulk, M.K., et al. "Synthesis and characterization of sol–gel derived lanthanum" J. Mater. Res., vol. 10, No. 1, p. 76, (1995).
Demian, S.E., "Optical and electrical properties of transparent conducting ZnO films prepared by spray pyrolysis" Journal of Materials Science, Material in Electronics, vol. 5, pp. 360–363, (1994).
Kanda, F., et al. "Efficacy of novel hybrid powders to quench body malodors" J. Soc. Cosmet. Chem. vol. 41, pp. 197–207, (1990).
Kanda, F., et al. "Elucidation of Body Odour Components and Development of Novel Deodorants Against Them" Fragrance Journal, No. 9, pp. 83–85, (1992).
Jezequel, D., et al. "Submicrometer zinc oxide particles: Elaboration in polyol medium and morphological characteristics" J. Mater. Res., vol. 10, No. 1, pp. 77–83, (1995).
Teo, C.K., et al. "Superplastic behaviour of a ceramic–based kappa/alpha Fe–10Al–1.9C material" Journal of Materials Science, vol. 29, pp. 6581–6586, (1994).

*Primary Examiner*—Shelley A. Dodson
(74) *Attorney, Agent, or Firm*—Stephan P. Williams

(57) ABSTRACT

A deodorant composition for topical application, which comprises a plurality of particles dispersed and a carrier, each particle comprising a glass microsphere at least partially coated with zinc oxide, a zinc salt, or any mixture of two or more thereof.

25 Claims, 2 Drawing Sheets

DEODORANT COMPOSITIONS

This is a continuation of International Application No. PCT/US500/04497 filed on Feb. 23, 2000.

BACKGROUND

This invention relates to deodorant compositions.

Zinc oxide is known to have bactericidal properties, and has been widely used in deodorant compositions. It is believed to work by the zinc ions of the zinc oxide going into solution in the outer layer of the skin, where they kill microorganisms by preventing enzymes therein from functioning properly.

Inhalation of zinc oxide particles smaller than about 10 micrometers can cause adverse reactions in humans and animals. For this reason, many countries have adopted Health and Safety legislation forbidding the use of zinc oxide particles smaller than 10 micrometers in aerosols. This places a lower limit on the size of zinc oxide particles that can be used in aerosol deodorant compositions.

Although zinc oxide particles can easily be made to a size greater than 10 micrometers, such particles appear as a white powder and are considered unsightly. In order to avoid this white appearance it would be necessary to use a zinc oxide particle size below 10 micrometers, but this would not be permitted under the legislation referred to above.

Spherical particles comprising a zinc oxide coating are known. Thus, U.S. Pat. No. 5,407,743 describes electromechanical devices such as transducers which comprise glass spheres of size 1 to 500 microns coated with zinc oxide. The zinc oxide coating is formed by applying a zinc oxide precursor to the spheres and then contacting the coated spheres with an oxidizing agent to form a zinc oxide coating on the spheres.

J. Soc. Cosmet. Chem., 41, 197—207 (May/June 1990) describes a mechanochemical process wherein fine particle zinc oxide is mixed with spherical resin cores to provide a hybrid powder of cores with their surfaces uniformly covered with zinc oxide. The powder has deodorizing qualities.

SUMMARY OF THE INVENTION

We have now devised some deodorant compositions containing zinc oxide, or a zinc salt, whereby one or more of a number of advantages over prior known compositions can be obtained including, if desired, the advantage of substantially transparent zinc oxide (or zinc salt) without the need to use particles having a size below 10 micrometers.

According to one aspect of the invention, we provide a deodorant composition for topical application, which comprises a plurality of particles which each comprise a glass microsphere at least partially coated with a zinc compound sintered to the glass microsphere, the zinc compound being selected from zinc oxide, a zinc salt or any mixture of two or more thereof, said particles being dispersed in a carrier.

DESCRIPTION OF THE PREFERRED EMBODIMENTS

Figure 1:
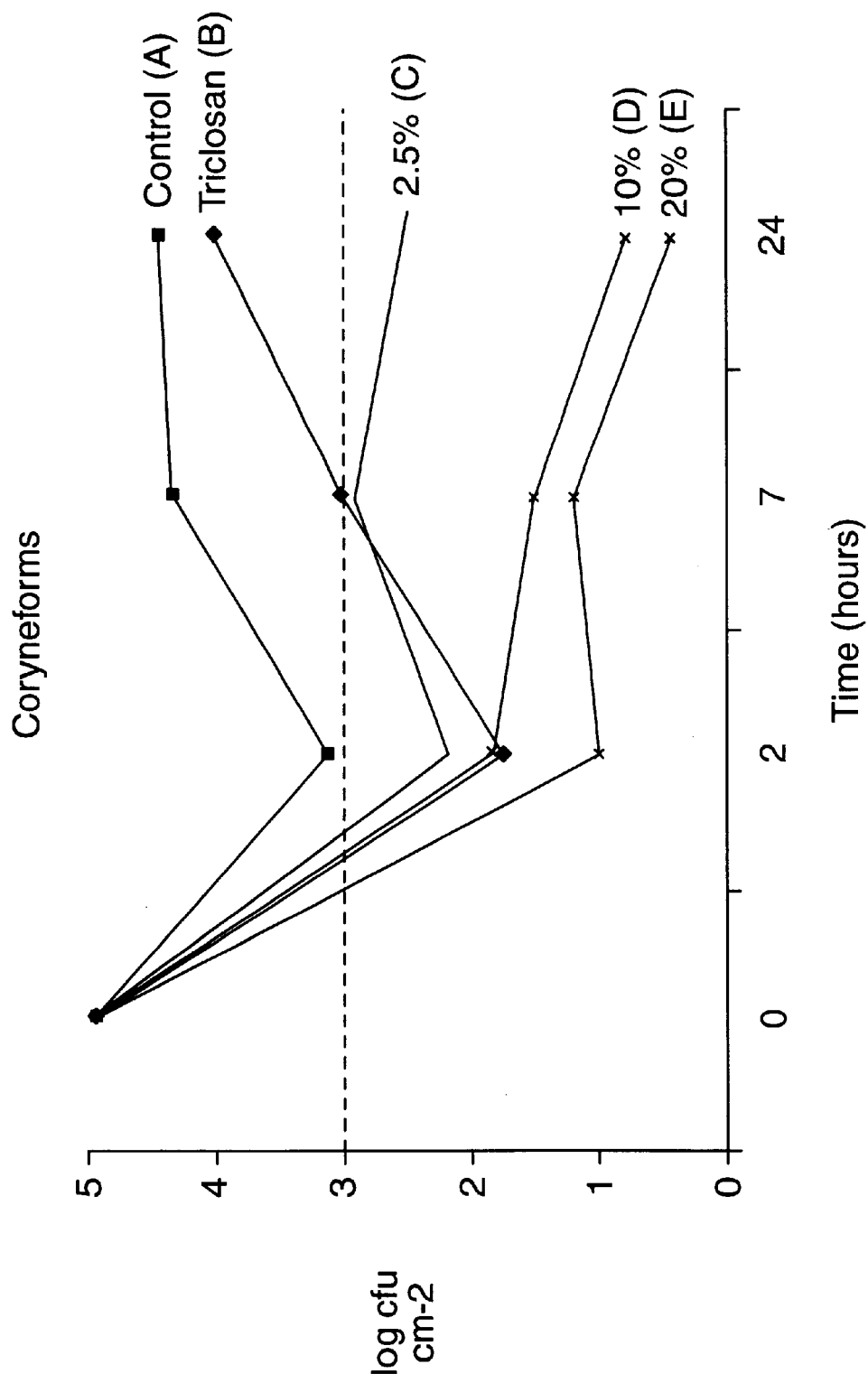
FIG. 1 is a graph of log [colony forming units per $cm^2$] versus time for coryneform bacteria.

In the compositions of the present invention, the microspheres may be coated only with zinc oxide, or with both zinc oxide and a zinc salt, or with a salt alone (mixtures of two or more salts can be used). We prefer that the coating comprises zinc oxide and a salt since then the bactericidal activity of the zinc oxide is enhanced and the product remains active for an extended period. If the coating consists only of one or more zinc salts with no zinc oxide present, the active bactericidal life of the coating is usually relatively short. If the coating consists of zinc oxide alone, its bactericidal activity is not as great as when a zinc salt is also present.

The preferred zinc salts are those which can be made by reacting a zinc oxide coating with an acid to form the salt in situ on the microspheres. Preferably, the zinc salts are only sparingly soluble in water so that they are not quickly removed by contact with water. The preferred salts are made by reacting the zinc oxide with a carboxylic acid or a substituted phenol. Examples of the preferred salts are the acetate, pidolate, pyrrolidone-5-carboxylate, cinnamate, citrate and glycinate, but these are merely illustrative of the many possible salts which can advantageously be used.

The compositions according to the invention may also contain at least one further bactericide in addition to the zinc oxide or zinc salt.

The colour of the particles depends upon the colour of the glass microsphere core, because the layer of the zinc compound (by which we mean zinc oxide and/or one or more zinc salts) will be substantially transparent, provided that it is thin enough. This makes it possible to provide a deodorant composition which has the bactericidal advantages of zinc oxide without the white appearance normally associated with deodorant compositions containing zinc oxide particles larger than 10 microns. In order to comply with legislation relating to the size of zinc oxide particles in aerosols, the glass microspheres would normally have a minimum diameter of about 10 micrometers, although for other uses, they may of course be smaller, eg. down to 5 micrometers or less. We have found that, in order to obtain good transparency, it is preferable that the diameter of the glass microspheres should not exceed about 50 micrometers. However, greater diameters can be used, for example up to 150 micrometers or more.

In order to prepare the zinc oxide coated microspheres of the invention, it is important to control the reaction temperature closely. In accordance with another aspect of the invention, we provide a method of coating glass microspheres with zinc oxide, which method comprises heating an agitated mixture of the glass microspheres and a zinc compound in a liquid reaction medium to form a milky suspension of colloidal zinc oxide, and further heating the suspension to 190° C. to 200° C. to deposit the zinc oxide as an adherent coating sintered on the glass microspheres. We have found that if the temperature is outside this range, then either the yield of zinc oxide or the adherence of the coating, or both, will be generally unsatisfactory.

We have also found that heating in two stages, at two different temperatures, provides the best combination of adhesion and yield. Accordingly, we prefer to form the milky suspension by heating the mixture to 140° C. to 160° C., preferably for 1 to 3 hours. Then, we prefer to heat for a further 1 to 3 hours to deposit said coating at 190° to 200° C.

The method of the invention is carried out in a liquid reaction medium. This should have a high enough dielectric constant that it dissolves the zinc compound, and also a high enough boiling point to allow the high temperatures to be obtained to produce the zinc oxide and allow sintering of the coating on the surface of the glass microspheres. Among the preferred such solvents are the glycols, particularly (but not exclusively) diethylene glycol, tetraethylene glycol and poly (ethylene glycol). Diethylene glycol has a dielectric constant of 31.7 at 20° C. and a boiling point of 245° C. Poly(ethylene glycol) of molecular weight 300 has a dielectric constant of 37.7 at 20° C. and a boiling point of 198° C.

Any zinc compound can be used which will hydrolyse in the process to yield zinc oxide. The preferred zinc compounds are the carboxylates (other than the oxalate), most preferably the acetate. The chloride and sulphate are not used since zinc oxide is not readily formed therefrom in glycol solutions. As will be clear to those skilled in the art, the suitability of any particular zinc compound can be ascertained by routine trial and experiment.

When the zinc compound used is zinc acetate dihydrate, we prefer the glycol to be diethylene glycol, tetraethylene glycol or poly(ethylene glycol) of molecular weight 300 (PEG Mr 300). The use of these glycols leads to the formation of the zinc oxide as a single phase which is preferred. Other glycols can also be used although some may lead to the formation of the less desirable impure multiphase compounds. In general, any glycol can be used but we prefer to use one of the above three or any mixture of two or all three thereof.

According to a further feature of the invention, when it is desired that the coating on the microspheres should comprise a zinc salt, the salt can be formed in situ by reacting the zinc oxide coating with an acid. We prefer to form a layer of a zinc salt at the exposed surface of the zinc oxide, so that the product comprises microspheres with a zinc oxide coating having zinc salt thereon. However, if desired, the whole of the zinc oxide can be reacted with acid so that the product then comprises microspheres with zinc salt coatings (and no zinc oxide).

The zinc oxide coating of the invention comprises submicron primary particles or crystallites of the zinc oxide with diameters in the region of, for example, about 30 nm. These colloidal particles aggregate and form particulate clusters with diameters in the range of about 0.3 to about 0.5 micrometers. The size of the primary particles can be controlled by varying the reaction temperature as described more fully hereinafter.

It is usually preferred for the compositions of the invention to be transparent, in which case the glass microspheres are preferably substantially transparent. However, there may be circumstances in which it is desirable for the composition to have a particular colour. It is possible to provide the composition with a desired colour by using glass microspheres having the desired colour.

The compositions according to the invention may be provided in any convenient form suitable for topical application. For example, the compositions may be provided in the form of an aerosol, roll-on, gel, stick, cream, lotion or pump spray formulation.

In the compositions of the invention, the carrier is preferably a dermatologically acceptable vehicle such as, for example, a polyhydric alcohol, a silicone, ethanol, water etc. or any mixture of two or more thereof.

The compositions of the invention may be formulated into topical compositions such as aerosols, pump sprays, roll-ons, lotions, creams, gels, sticks etc. In particular, aqueous suspensions of the zinc oxide particles and salts may be directly utilized in oil-in-water and water-in-oil emulsions, such as the currently popular clear gel formulations, or in other aqueous based compositions such as aqueous based roll-ons. The compositions of the invention may be formulated into any known type of topical composition which utilizes powdered salts including, in particular, aerosol, liquid roll-on, cream and solid stick formulations in which the powdered salt is suspended in an anhydrous, dermatologically acceptable carrier, particularly a carrier comprising a silicone.

It will be appreciated that the precise formulation of the deodorant compositions will depend upon the type of deodorant composition which is desired. Thus, an aerosol formulation will contain predominantly a propellant, such as CAP30 propellant; a stick type formulation will typically contain predominantly propylene glycol; a roll-on formulation will typically contain predominantly cyclomethicone; and a gel formulation will typically contain predominantly water and propylene glycol. The deodorant compositions according to the invention may include any of the materials conventionally used in deodorant formulations. The compositions of the invention may comprise, in addition to the zinc oxide coated particles, other different particles.

The deodorant compositions according to the invention will contain sufficient zinc compound coated microspheres to reduce or prevent malodour when applied to the skin. Typically, they will contain from 0.1 to 25 wt % of the zinc compound coated microspheres. It is preferred that the compositions comprise 5 to 15 wt % of the zinc compound coated microspheres, more preferably up to about 10 wt %.

In accordance with another aspect of the invention, we provide an aerosol, roll-on, gel or pump spray device which includes a deodorant composition as described above.

According to another aspect of the invention we provide the use of particles comprising glass microspheres coated with a zinc compound as a deodorant in compositions for topical application. The particles may have the features of the particles of the deodorant composition described above.

The invention will now be described with reference to the following Examples.

EXAMPLE 1

Zinc acetate dihydrate (44 g) and sodalime glass microspheres (22 g) were added to a 1 liter reaction kettle containing 500 ml of diethylene glycol. The sodalime glass microspheres were obtained from Croxton & Gary under the trade name Spheriglass 2000 cpo, and had a diameter in the range 10 to 50 micrometers.

A flanged lid with a propeller type stirring paddle was placed over the reaction kettle. The kettle was then placed in an oil bath and subjected to a heating cycle of 2 hours at 150° C. followed by 2 hours at 190° C. On completion of the heating, the kettle was removed from the oil bath and the diethylene glycol was decanted off. The remaining zinc oxide coated glass microspheres were filtered and washed in ethanol. The coated microspheres were then dried at room temperature.

A sample of the microspheres was coated with gold, then subjected to SEM analysis. This showed that the zinc oxide is present as clusters of primary particles.

These zinc oxide clusters consist of aggregates of much smaller zinc oxide primary particles. The primary particles are nm sized, and they are aggregated together to form the larger sub-micron sized (eg. 0.3–0.5 $\mu$m) clusters.

The zinc oxide coated microspheres prepared by this method can be used to form a variety of deodorant compositions, as exemplified in Examples 2 to 5.

EXAMPLE 2

An aerosol type deodorant was prepared from the following materials:

| | |
|---|---|
| CAP30 propellant | 80 wt % |
| ZnO coated microspheres | 2.5 wt % |
| Ethanol | 11.5 wt % |
| Volatile silicone DC245 | 6 wt % |

EXAMPLE 3

A stick type deodorant was prepared from the following materials:

| | |
|---|---|
| Water | 12 wt % |
| Propylene glycol | 71 wt % |
| Sodium stearate | 8 wt % |
| ZnO coated microspheres | 8 wt % |
| Perfume | 1 wt % |

EXAMPLE 4

A suspension roll-on type deodorant was prepared from the following materials:

| | |
|---|---|
| Cyclomethicone | 86 wt % |
| ZnO coated microspheres | 8 wt % |
| Ethanol | 2.5 wt % |
| Quaternium 18 Hectorite | 2 wt % |
| Perfume | 1.5 wt % |

EXAMPLE 5

A gel type deodorant was prepared from the following materials:

| | |
|---|---|
| Water | 25.25 wt % |
| Sorbitol | 14 wt % |
| Ethanol | 12 wt % |
| Propylene glycol | 22.5 wt % |
| ZnO coated microspheres | 8 wt % |
| Dimethicone (DC-225) | 10 wt % |
| Cyclomethicone & dimethicone copolyol | 8 wt % |
| Perfume | 0.25 wt % |

EXAMPLE 6

A modified zinc oxide coating was prepared by reacting the ZnO coated microspheres with eugenol (4-allyl-2-methoxyphenol). The following formulation was prepared:

| | |
|---|---|
| Acetone | 89 wt % |
| Eugenol | 5 wt % |
| ZnO coated microspheres | 4 wt % |
| Distilled water | 2 wt % |

The formulation was stirred at room temperature for 48 hours, then the modified ZnO coated microspheres were isolated by filtration, washed and dried at room temperature.

EXAMPLE 7

A modified zinc oxide coating was prepared by reacting the ZnO coated microspheres with pyrrolidone-5-carboxylic acid. The following formulation was prepared:

| | |
|---|---|
| Pyrrolidone-5-carboxylic acid | 5 wt % |
| ZnO coated microspheres | 4 wt % |
| Distilled water | 91 wt % |

The formulation was stirred at room temperature for 48 hours, then the modified ZnO coated microspheres were isolated by filtration, washed and dried at room temperature.

EXAMPLE 8

An in-vivo method, known as the Williamson and Kligman surface scrub, was used to demonstrate the antimicrobial properties of the following five compositions:

(A) A control composition comprising ethanol/volatile silicone (B) A composition comprising ethanol/volatile silicone and 0.3 wt % of a well known deodorant known as Triclosan (2,4,4'-trichloro-2-hydroxybiphenyl ether). This concentration is the highest amount of Triclosan that can be used without skin irritation.

(C) A composition according to the invention comprising ethanol/volatile silicone containing 2.5 wt % of the zinc oxide coated particles obtained by the method of Example 1.

(D) A composition according to the invention comprising ethanol/volatile silicone containing 10 wt % of the zinc oxide coated particles obtained by the method of Example 1.

(E) A composition according to the invention comprising ethanol/volatile silicone containing 20 wt % of the zinc oxide coated particles obtained by the method of Example 1.

In all the above compositions, the ratio of ethanol to silicone was 70/30, and there were substantially no other components present except those indicated.

The test was designed to measure the growth of the bacteria staphylococci and coryneforms in the axilla of each member of a group of participants. These two types of bacteria are primarily responsible for the development of odours.

Initially, a sample of bacteria was removed from the axilla of each participant. A 0.5 ml aliquot of various deodorant compositions was then applied to the axilla of the participants, and further bacteria samples were removed after 2, 7 and 24 hours. The level of coryneforms and staphylococci in each sample were then measured.

Figure 2:
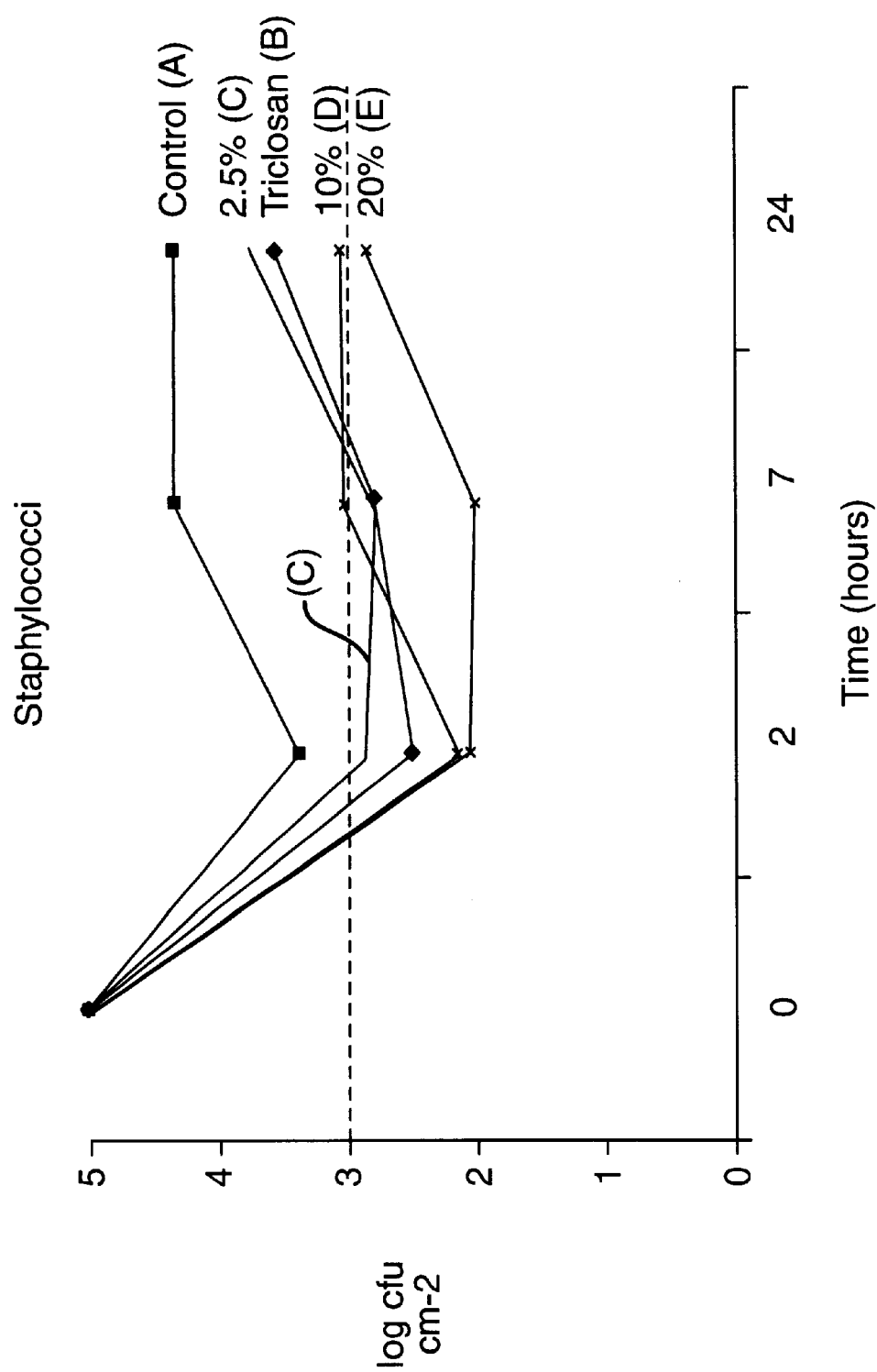
FIG. 2 is a graph of log [colony forming units per $cm^2$] versus time for staphylococci bacteria.

Bacteria level counts were obtained for each sample, and the change in bacteria levels with time is shown in FIGS. 1 and 2. The black dotted line represents the level of bacteria at which odours start to become detectable. It is clear that compositions (C), (D) and (E) are substantially more effective than compositions (A) or (B). The results show that compositions (C), (D) and (E) were effective against coryneforms for up to 24 hours. Furthermore, the compositions (C), (D) and (E) did not cause any skin irritation.

What is claimed is:

1. A deodorant composition for topical application, which comprises a plurality of particles dispersed in a dermatologically acceptable carrier vehicle, wherein each of said particles consists essentially of a glass microsphere having a diameter of from 5 to 150 micrometers at least partially coated with a zinc compound sintered to the glass microsphere, the zinc compound being selected from the group consisting of zinc oxide, a zinc salt and a mixture of at least two thereof.

2. A composition according to claim 1, wherein the zinc compound comprises zinc oxide and a zinc salt.

3. A composition according to claim 2, wherein the zinc salt is selected from the group consisting of zinc pidolate, zinc acetate, zinc eugolinate, zinc pyrrolidone-5-carboxylate, zinc cinnamate, zinc citrate and zinc glycinate.

4. A composition according to claim 2, wherein the zinc salt is formed by contacting a zinc oxide coating on the microspheres with carboxylic acid or a phenol.

5. A composition according to claim 1, which also contains at least one further bactericide in addition to the zinc oxide.

6. A composition according to claim 1, wherein the glass microspheres have a diameter of from 10 to 50 micrometers.

7. A composition according to claim 1, wherein the zinc oxide or zinc salt is present in the coating in particle clusters of a diameter from 0.3 to 0.5 micrometers.

8. A composition according to claim 6, wherein said particles are substantially transparent.

9. A composition according to claim 1, wherein the carrier vehicle is selected from the group consisting of a polyhydric alcohol, a silicone, ethanol, water and a combination of at least two thereof.

10. A composition according to claim 1, which contains from 0.1 to 25 wt. % of the particles.

11. A composition according to claim 1, which contains from 0.1 to 10% by weight of said particles.

12. A composition according to claim 1, which is in the form selected from the group consisting of an aerosol, roll-on, gel, stick, cream, lotion and pump spray formulation.

13. An aerosol, roll-on, gel, stick, cream, lotion or pump spray device which includes a composition according to claim 1.

14. An aerosol, roll-on, gel, stick, cream, lotion or pump spray device which includes a composition according to claim 2.

15. A method of preventing or reducing malodour which comprises applying to the skin a deodorant composition as claimed in claim 1.

16. A method of coating glass microspheres which consists essentially of heating an agitated mixture of glass microspheres and a zinc compound in a liquid reaction medium to form a milky suspension of colloidal zinc oxide, and further heating the suspension to 190° C. to 200° C. to deposit the zinc oxide as an adherent coating sintered on the glass microspheres.

17. A method according to claim 16, wherein the mixture is heated to 140° C. to 160° C. to form said milky suspension.

18. A method according to claim 16, wherein the liquid reaction medium comprises a glycol.

19. A method according to claim 18, wherein the glycol is selected from the group consisting of diethylene glycol and poly(ethylene glycol).

20. A method according to claim 16, wherein the mixture is heated for 1 to 3 hours to form said suspension, and for a further 1 to 3 hours to deposit said coating.

21. A method according to claim 17, the mixture is heated for 1 to 3 hours to form said suspension, and for a further 1 to 3 hours to deposit said coating.

22. A method according to claim 16, wherein the zinc oxide coating is contacted with carboxylic acid or a phenol to form a zinc salt thereon.

23. A method according to claim 22, wherein only part of the zinc oxide coating is converted to a zinc salt.

24. A method according to claim 22, wherein the carboxylic acid is selected from the group consisting of pidolic acid, acetic acid, euginol, pyrrolidone-5-carboxylic acid, cinnamic acid, citric acid and glycine.

25. A method according to claim 22, wherein after forming the zinc salt, the microspheres are washed with water without removal of the salt.

* * * * *